United States Patent [19]

Hoffman et al.

[11] Patent Number: 4,808,597

[45] Date of Patent: Feb. 28, 1989

[54] METHOD FOR INHIBITING THE DEGRADATION OF CARTILAGE

[75] Inventors: William W. Hoffman, Mystic; Allen R. Kraska, East Lyme, both of Conn.

[73] Assignee: Pfizer Inc., New York, N.Y.

[21] Appl. No.: 201,500

[22] Filed: Jun. 2, 1988

Related U.S. Application Data

[63] Continuation of Ser. No. 511,037, Jul. 5, 1983, abandoned.

[51] Int. Cl.[4] ............... A61K 31/35; A61K 31/38; A61K 31/47
[52] U.S. Cl. .................. 514/311; 514/314; 514/381; 514/382; 514/432; 514/456; 546/165; 546/166; 548/251; 549/23; 549/398
[58] Field of Search ............ 546/165, 166; 548/251; 549/23, 398; 514/311, 314, 381, 382, 432, 456

[56] References Cited

FOREIGN PATENT DOCUMENTS 2010836  7/1979  United Kingdom .

OTHER PUBLICATIONS

Loeliger et al., Eur. J. Med. Chem., vol. 15, pp. 9–15 (1980).

Primary Examiner—Richard L. Raymond
Attorney, Agent, or Firm—Peter C. Richardson; J. Trevor Lumb

[57] ABSTRACT

Certain carboxylic acids of the formula

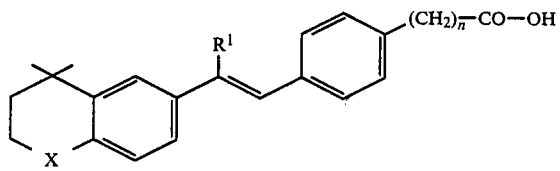

and the pharmaceutically-acceptable salts thereof, and certain esters and amides thereof, are useful for inhibiting the degradation of articular cartilage when administered to a mammalian subject afflicted with an arthritic disease. X is O, S, SO, $SO_2$, NH, $NCH_3$ or $NCOCH_3$; and n is zero or one.

12 Claims, No Drawings

METHOD FOR INHIBITING THE DEGRADATION OF CARTILAGE

CROSS-REFERENCE TO RELATED APPLICATION

This application is a continuation of application Ser. No. 06/511,037, filed July 5, 1983 now abandoned.

BACKGROUND OF THE INVENTION

This application relates to new chemical compounds. More particularly, it relates to new chemical compounds which have the ability to inhibit the degradation of cartilage, when administered to a mammalian subject afflicted with an arthritic disease.

Cartilage is a proteinaceous material found in the joints of mammals. It is an elastic, spongy substance which covers the articular surfaces of the bones within the synovial cavity. The presence of cartilage, with its special properties of compressibility, elasticity and deformability, permits joints to carry out their two major functions, which are to bear weight and facilitate locomotion.

However, in certain disease states of mammals, such as osteoarthritis or hypertrophic arthritis, degeneration of joints occurs, and a major component of this degeneration is loss, or degeneration, of cartilage. It is an object of this invention to provide a method for inhibiting the degradation of cartilage in a joint of a mammalian subject.

SUMMARY OF THE INVENTION

This invention provides new chemical compounds of the formula

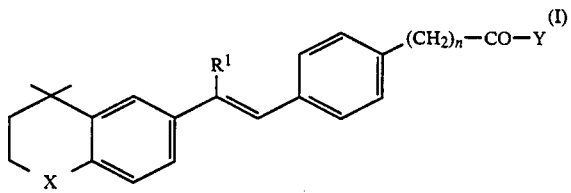

and the pharmaceutically-acceptable acid addition salts thereof and the pharmaceutically-acceptable base salts thereof, wherein X is selected from the group consisting of O, S, SO, $SO_2$ and $NR^2$;

$R^1$ is selected from the group consisting of H and $CH_3$;

Y is selected from the group consisting of OH, $OR^3$ and $NHR^4$; and n is zero or one; wherein.

$R^2$ is selected from the group consisting of H, $CH_3$ and $CO-CH_3$;

$R^3$ is selected from the group consisting of alkyl having 1 to 5 carbons and phenyl;

and $R^4$ is selected from the group consisting of H, alkyl having 1 to 5 carbons, phenyl, hydroxyphenyl and 5-tetrazolyl.

Further, this invention provides a method for inhibiting the degradation of cartilage in a joint of a mammalian subject afflicted with an arthritic disease, which comprises administering to said subject a compound of formula I, or a pharmaceutically-acceptable salt thereof.

Yet further, this invention provides pharmaceutical compositions comprising a compound of the formula I, or a pharmaceutically-acceptable salt thereof, and a pharmaceutically-acceptable carrier.

Preferred compounds of the invention are the compounds of formula I, wherein X is O. Within this preferred group, particularly preferred compounds are those in which R is $CH_3$. An especially preferred individual compound of this invention is 4-[(E)-2-(4,4-dimethyl-6-chromanyl)-2-methylvinyl]benzoic acid, the compound of formula I, wherein X is O, $R^1$ is $CH_3$, Y is OH and n is zero.

DETAILED DESCRIPTION OF THE INVENTION

The compounds of formula I, wherein X is O, S, SO, $SO_2$ or $NCOCH_3$, $R^1$ is H or $CH_3$, Y is $OR^3$ and n is zero or one, wherein $R^3$ is alkyl having 1 to 5 carbon or phenyl, can be prepared by reacting a phosphonium halide of the formula

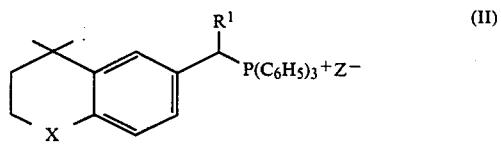

wherein Z is chloro or bromo, with the appropriate aldehyde of the formula

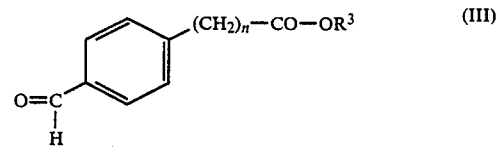

This is a typical Wittig reaction and it can be carried out in the normal manner for this type of transformation. However, a particularly convenient way of condensing II with III involves contacting substantially equimolar amounts of II and III in an epoxyalkane having 3 to 6 carbons at a temperature in the range from 30° to 100° C., and preferably at about 60° C. A particularly convenient epoxyalkane for use in this transformation is 1,2-epoxybutane. The reaction time varies according to the reaction temperature, but at about 60° C. reaction times of a few days, e.g. three days, are commonly used. At the end of the reaction, the product can be isolated by standard methods. For example, the product can be isolated by removing the epoxyalkane by evaporation in vacuo. The crude product thus obtained can be purified by standard methods such as recrystallization or chromatography, if desired.

The compounds of formula I, wherein X is O, S, SO or $SO_2$, R is H or $CH_3$, Y is OH and n is zero or one, can be prepared from the corresponding compound of formula I, wherein Y is $OR^3$ and $R^3$ is alkyl having 1 to 5 carbon atoms or phenyl, by hydrolysis. This is normally carried out by treating said compound of formula I, wherein Y is $OR^3$, with an excess of an aqueous solution of an alkali metal hydroxide, e.g. sodium or potassium hydroxide, or an alkaline earth metal hydroxide, e.g. magnesium or barium hydroxide, or an alkali metal carbonate, e.g. sodium or potassium carbonate. A cosolvent such as a lower alkanol, e.g. methanol or ethanol, can be added if desired. The reaction is usually run at a temperature in the range from 40° to 100° C., and preferably about 80° C. It usually takes a few hours, e.g. two hours, to reach completion. The product is then isolated by standard methods. For example, in one method, the cosolvent is removed by evaporation, the resulting mixture is acidified, and then the product is extracted into a volatile, organic solvent which is not miscible with water. Finally, the product is recovered by solvent evaporation. It can be purified by standard techniques, such as recrystallization.

The compounds of the formula I, wherein X is NH, $R^1$ is H or $CH_3$, Y is OH and n is zero or one, are prepared from the corresponding compound of formula I, wherein X is $NCOCH_3$ and Y is OH or $OR^3$, wherein $R^3$ is alkyl having 1 to 5 carbons or phenyl, by hydrolysis. This hydrolysis is carried out in exactly the same manner that was described earlier for preparation of a compound of formula I, wherein X is O, S, SO or $SO_2$, $R^1$ is H or $CH_3$, Y is OH and n is zero or one.

The compounds of formula I, wherein X is $NCOCH_3$, $R^1$ is H or $CH_3$, Y is OH and n is zero or one, are prepared by hydrolysis of the corresponding compound, wherein Y is $OR^3$, wherein $R^3$ is alkyl having 1 to 5 carbons or phenyl. This is carried out by treating the starting material with an excess of an aqueous solution of an alkali metal hydroxide, e.g. sodium or potassium hydroxide, or an alkaline earth metal hydroxide, e.g. magnesium or barium hydroxide, or an alkali metal carbonate, e.g. sodium or potassium carbonate. Also a cosolvent such as a lower alkanol, e.g. methanol or ethanol, can be added if desired. However, in order to avoid hydrolysis of the $NCOCH_3$ moiety, the reaction is run at a temperature in the range from 15° to 30° C., and preferably at about 25° C. At about 25° C., the reaction is normally complete within about 48 hours, and then the product can be isolated in exactly the same manner as described earlier for a compound of formula I, wherein X is O, S, SO or $SO_2$, $R^1$ is H or $CH_3$, Y is OH and n is zero. or one.

The compounds of formula I, wherein X is SO, $R^1$ is H or $CH_3$, Y is OH, $OR^3$ or $NHR^4$, and n is zero or one, wherein $R^3$ is alkyl having 1 to 5 carbons atoms or phenyl and $R^4$ is H, alkyl having 1 to 5 carbon atoms, phenyl, hydroxyphenyl or 5-tetrazolyl, can also be prepared from the corresponding compound of formula I, wherein X is S. This is achieved by oxidation of the sulfide moiety to a sulfoxide moiety, and a variety of reagents known in the art for this kind of transformation can be used. However, particularly convenient conditions for this purpose are the use of sodium metaperiodate in aqueous dioxane at about 0° C.

In like manner, the compounds of formula I, wherein X is $SO^2$, $R^1$ is H or $CH_3$, Y is OH, $OR^3$ or $NHR^4$, and n is zero or one, wherein $R^3$ is alkyl having 1 to 5 carbons atoms or phenyl and $R^4$ is H, alkyl having 1 to 5 carbon atoms, phenyl, hydroxyphenyl or 5-tetrazolyl, can also be prepared from the corresponding compound of formula I, wherein X is S. This is achieved by oxidation of the sulfide moiety to a sulfone moiety, and a variety of reagents known in the art for this kind of transformation can be used. However, particularly convenient conditions for this purpose are the use of a peroxy carboxylic acid, such as 3-chloroperbenzoic acid, in a reaction-inert organic solvent, such as chloroform.

The compounds of formula I, wherein X is $NCH_3$, $R^1$ is H or $CH_3$, Y is OH, $OR^3$ or $NHR^4$, and n is zero or one, wherein $R^3$ is alkyl having 1 to 5 carbons atoms or phenyl and $R^4$ is H, alkyl having 1 to 5 carbon atoms, phenyl, hydroxyphenyl or 5-tetrazolyl, can be prepared from the corresponding compound of formula I, wherein X is NH. This can be achieved by reductive methylation, and a convenient method involves treating the compound of formula I, wherein X is NH, with an excess of formaldehyde in refluxing formic acid.

The compounds of formula I, wherein X is O, SO, $SO_2$ or $NR^2$, $R^1$ is H or CH and Y is $NHR^4$, wherein $R^2$ is $COCH_3$ and $R^4$ is hydrogen, alkyl having 1 to 5 carbons, phenyl, hydroxyphenyl or 5-tetrazolyl, can be prepared from the corresponding compound of formula I, wherein Y is OH. This is achieved by activation of the carboxy group, e.g. by mixed anhydride formation, followed by reaction with an amine of formula $R^4\text{-}NH_2$. Thus, formation of the mixed anhydride involves suspending or dissolving an appropriate carboxylate salt of the carboxylic acid of formula I in a reaction-inert organic solvent, and then adding to this suspension or solution a reagent selected from pivaloyl chloride and lower-alkyl chloroformates. Appropriate salts are, for example, alkali metal salts, such as sodium or potassium salts, and amine salts, such as triethylammonium, pyridinium, N-ethylpiperidinium or N,N-dimethylanilinium salts. Appropriate solvents are those which serve to dissolve at least one of the reactants, and the mixed anhydride product, and do not adversely interact with the reactants or product. Examples of such solvents are chlorinated hydrocarbons, such as chloroform and methylene chloride; aromatic hydrocarbons, such as benzene, toluene and xylene; and ethers, such as diethyl ether, tetrahydrofuran and 1,2-dimethoxyethane. The reaction is usually carried out at a temperature in the range from about −50° C. to about 30° C., and preferably at about −25° C. At about −25° C., the reaction commonly requires less than one hour. The salt of the compound of formula I and the pivaloyl chloride or lower-alkyl chloroformate are normally present in roughly equimolar proportions, although in some instances a small excess of the acid chloride component is used. The product can be isolated simply by filtering off the insoluble materials, and then evaporating the solvent in vacuo to give the crude product. The latter can be used directly, or purified further by methods known in the art. If desired, however, the mixed anhydride product need not be isolated. It can be used in situ for reaction with the amine of formula $R^4\text{-}NH_2$. Reaction of the mixed anhydride with the amine of formula $R^4$-NH is usually carried out simply by contacting the reactants in an inert solvent, for about 0.1 to about 2.0 hours, at a temperature in the range from about −30° C. to about 30° C. and preferably at around −25° C. The same solvents identified above for mixed anhydride formation are useful for this reaction, and the reagents are usually used in approximately equimolar proportions. In the cases wherein this reaction is conducted in a water-immiscible solvent, the product is usually isolated by washing the reaction mixture with hydrochloric acid and then concentrating the organic solvent to dryness in vacuo, to give the crude product. The latter product can be purified further by well-known methods, such as chromatography or recrystallization.

The phosphonium halides of formula II are prepared by reaction of triphenylphosphine with the appropriate halo compound of the formula

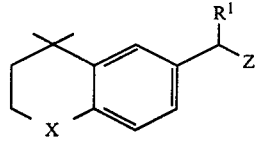 (IV)

wherein X is O, S, SO, SO or NCOCH, R¹ is H or CH₃, and Z is chloro or bromo, in refluxing toluene.

The halo compounds of formula IV, wherein Z is chloro, can be prepared from the corresponding alcohol of the formula

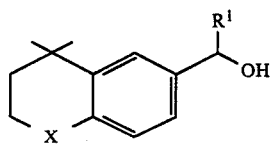 (V)

by reaction of an alcohol of formula V with thionyl chloride and pyridine, while the halo compounds of formula IV, wherein Z is bromo, can be prepared by reaction of an alcohol of formula V with phosphorus tribromide.

The halo compounds of formula IV can also be prepared by halogenation of the corresponding compound of the formula

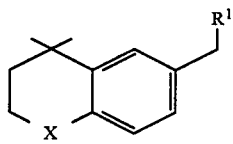 (VA)

using standard methods. For example, when Z is bromo the halogenation can be effected using N-bromosuccinimide in carbon tetrachloride.

The compounds of formula V, wherein X is O or S and R¹ is H or CH₃, can be prepared according to Scheme I.

SCHEME I

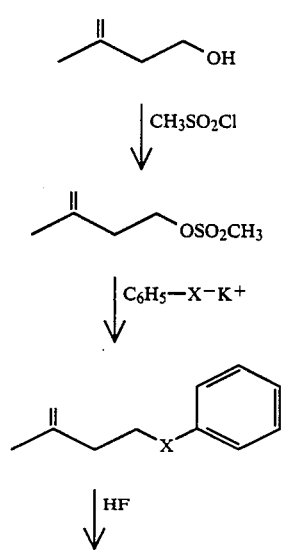

-continued
SCHEME I

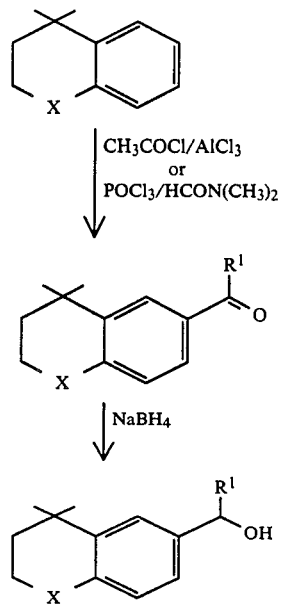

Firstly, 2-methyl-4-hydroxy-1-butene (X) is converted into its methanesulfonate ester (IX), using methanesulfonyl chloride. Displacement of the methanesulfonyloxy group with the potassium salt of phenol or thiophenol then affords 2-methyl-4-phenoxy-1-butene (VIII; X is O) or 2-methyl-4-thiophenoxy-1-butene (VIII; X is S). These latter materials are cyclized to 4,4-dimethylchroman (VII; X is O) or 4,4-dimethyl-thiochroman (VII; X is S) using liquid hydrogen fluoride. A compound of formula VII is then subjected to a Friedel-Crafts reaction (using acetyl chloride and aluminum chloride in carbon disulfide), to give the 6-acetyl derivative (VI; R¹ is CH₃), or it can be subjected to a Vilsmeier reaction (using phosphorus oxychloride and N,N-dimethylformamide) to give the 6-formyl derivative (VI; R¹ is H). Finally, the ketone or aldehyde of formula VI is reduced with sodium borohydride in methanol. This affords the desired alcohol of formula V.

An alcohol of formula V, wherein X is SO, can be prepared by oxidation of the corresponding compound, wherein X is S. This can be carried out in the same manner as that described for oxidation of a compound of formula I, wherein X is S, to a compound of formula I, wherein X is SO. Similarly, an alcohol of formula V, wherein X is SO₂, can be prepared by oxidation of the corresponding compound of formula V, wherein X is S, and the method described for the oxidation of a compound of formula I, wherein X is S to a compound of formula I, wherein X is SO₃ can be used.

The compounds of formula V, wherein X is NCOCH₃ and R¹ is H or CH₃, can be prepared according to Scheme II.

SCHEME II

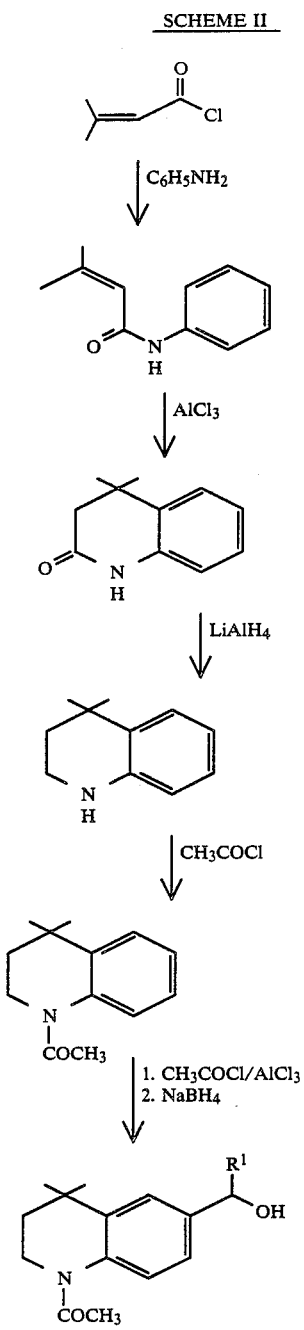

Firstly, 3-methylcrotonoyl chloride (XV) is reacted with aniline to give the amide (XIV), which is then cyclized using aluminum chloride in the absence of solvent. Reduction of the 2-oxo-1,2,3,4-tetrahydroquinoline thus obtained (XIII) with lithium aluminum hydride in diethyl ether then gives the amine of formula XII. This latter amine is acetylated, using acetyl chloride in pyridine, to give the amide of formula XI. A compound of formula XI is then subjected to a Friedel-Crafts reaction (using acetyl chloride and aluminum chloride in carbon disulfide), to give the 6-acetyl derivative, or it can be subjected to a Vilsmeier reaction (using phosphorus oxychloride and N,N-dimethylformamide) to give the 6-formyl derivative. Finally, the ketone or aldehyde thus obtained is reduced with sodium borohydride in methanol to give the desired alcohol of formula V.

The compounds of the formula I, wherein Y is OH, are acidic and they form base salts. All such base salts are within the scope of this invention. They can be prepared by conventional methods for carboxylic acid compounds. For example, they can be prepared readily and conveniently simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Basic agents suitably employed in salt formation belong to both the organic and inorganic types, and they include ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are amines, such as n-butylamine, cyclohexylamine, benzylamine, p-toluidine, octylamine, diethylamine, morpholine, pyrrolidine, piperidine, triethylamine, N-ethylpiperidine, N-methylmorpholine and 1,5-diazobicyclo[4.3.0]non-5-ene; hydroxides, such as sodium hydroxide; alkoxides, such as sodium methoxide and potassium methoxide; hydrides, such as calcium hydride and sodium hydride; and carbonates, such as potassium carbonate and sodium carbonate.

Additionally, the compounds of formula I, wherein X is NH or NCH$_3$, are basic and they will form acid-addition salts. All such acid-addition salts are within the scope of this invention. They can be prepared by conventional methods for amine compounds. For example, they can be prepared by contacting said compound of formula I, wherein X is NH or NCH$_3$, with a stoichiometric amount of the appropriate acid in an appropriate solvent. The salt can then be recovered by filtration, by precipitation with a non-solvent followed by filtration, or by evaporation of the solvent, as appropriate. Acid-addition salts of compounds of formula I, wherein X is NH or NCH$_3$, can be prepared from both inorganic and organic acids, and typical salts are the hydrochloride, hydrobromide, hydroiodide, sulfate, bisulfate, phosphate, acetate, maleate, fumarate, oxalate, lactate, tartrate, citrate, gluconate and 4-toluenesulfonate.

However, as will be appreciated by one with skill in the art, whenever it is intended to use a salt of a compound of formula I for administration to a mammalian subject, it is necessary to use a pharmaceutically-acceptable salt.

As indicated hereinbefore, the compounds of formula I, and the pharmaceutically-acceptable salts thereof, have the ability to inhibit the degradation of cartilage when they are administered to a mammalian subject afflicted with an arthritic disease. For this purpose, said compounds of formula I, and the pharmaceutically-acceptablessalts thereof, can be administered to a mammalian subject either alone, or, preferably, in combination with pharmaceutically-acceptable carriers or diluents, in a pharmaceutical composition, according to standard pharmaceutical practice. A compound can be administered orally or parenterally. Parenteral administration includes intravenous, intramuscular, subcutaneous and intraarticular administration.

In a pharmaceutical composition comprising a compound of formula I, or a pharmaceutically-acceptable salt thereof, the weight ratio of active ingredient to carrier will normally be in the range from 1:1,000 to 1:20, and preferably about 1:500. However, in any given case, the ratio chosen will depend on such factors as the solubility of the active component, the dosage contemplated and the precise route of administration.

For oral use of a compound of this invention, or a pharmaceutically-acceptable salt thereof of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, subcutaneous, intra-articular and intravenous use, sterile solutions of the active ingredient are usually prepared, and the pH of the solutions should be suitably adjusted and buffered. For intravenous use, the total concentration of solutes should be controlled to render the preparation isotonic.

When a compound of formula I or salt thereof is used to inhibit the degradation of cartilage in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 0.05 mg to 1.0 mg, in single or divided doses. On the other hand, it may be necessary to use dosages outside these limits in some cases.

The following examples are provided solely for the purpose of further illustration. Infrared spectra were measured as potassium bromide discs, and diagnostic absorption bands are reported in reciprocal centimeters (cm$^{-1}$). Proton nuclear magnetic resonance spectra ($^1$H NMR) were measured in deuterochloroform (CDCl$_3$) or perdeutero methanol (CD$_3$OD), and peak positions are expressed in parts per million (ppm) downfield from internal tetramethylsilane. The following abbreviations for peak shapes are used: s, singlet; bs, broad singlet; d, doublet; t, triplet; q, quartet; and m, multiplet.

EXAMPLE 1

Methyl 4-[(E)-2-(4,4-Dimethyl-6-chromanyl)-2-methylvinyl]-benzoate

A solution of 2.0 g (3.8 mmol) of 1-(4,4-dimethyl-6-chromanyl)ethyltriphenylphosphonium bromide and 630 mg (3.8 mmol) of methyl 4-formylbenzoate in 100 ml of 1,2-epoxybutane was heated under reflux for 72 hours. The reaction mixture was then concentrated in vacuo to an oil. The oil was purified by column chromatography on silicic acid, eluting with ether-hexane (1:9). This afforded mg (27% yield) of the title compound as a solid, mp 92°-95° C.

The $^1$H NMR spectrum of the product (in CDCl$_3$) showed absorptions at 1.38 (s, 6H), 1.82 (t, 2H, J=5 Hz), 2.23 (d, 3H, J=1 Hz), 3.88 (s, 3H), 4.15 (t, 2H, J=5 Hz), 6.67 (t, 1H, J=1 Hz), 6.67 (d, 1H, J=8 Hz), 7.07-7.4 (m, 4H) and 7.83 (d, 2H, J=8 Hz) ppm.

EXAMPLE 2

Reaction of the appropriate phosphonium salt with the requisite aldehyde, according to the procedure of Example 1, afforded the following compounds:

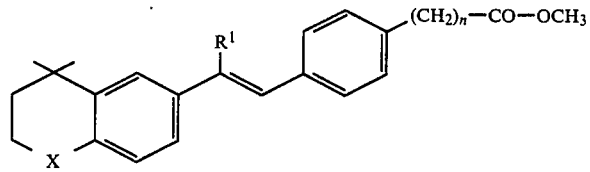

| | | | Melting Point | Analysis Calculated | | | Analysis Found | | | |
|---|---|---|---|---|---|---|---|---|---|---|
| X | R$^1$ | n | (°C.) | C | H | S | C | H | S | NMR (ppm) (in CDCl$_3$) |
| O | H | 0 | 138-139 | 78.23 | 6.88 | | 78.12 | 7.04 | | 1.35 (s, 6H), 1.78 (t, 2H, J=5 Hz), 3.87 (s, 3H), 4.15 (t, 2H, J=5 Hz), 6.63-7.32 (m, 5H), 7.67 (d of d, 4H, J=8 Hz and 30 Hz) |
| O | CH$_3$ | 1 | 85-86 | 78.82 | 7.48 | | 78.64 | 7.36 | | 1.37 (s, 6H), 1.80 (t, 2H, J=5 Hz), 2.22 (s, 3H), 3.58 (s, 2H), 3.65 (s, 3H), 3.82 (t, 2H, J=5 Hz), 6.62 (s, 1H), 6.77-7.0 (m, 7H) |
| S | CH$_3$ | 0 | 123-124.5 | 74.96 | 6.86 | 9.10 | 75.14 | 6.96 | 8.92 | 1.37 (s, 6H), 1.97 (t, 2H, J=6 Hz), 2.27 (s, 3H), 3.03 (t, 2H, J=6 Hz), 3.90 (s, 3H), 6.77 (s, 1H), 6.97-8.08 (m, 7H) |

EXAMPLE 3

By reacting the appropriate phosphonium bromide of formula II with the requisite aldehyde of formula III, using the procedure of Example 1, the following compounds can be prepared:

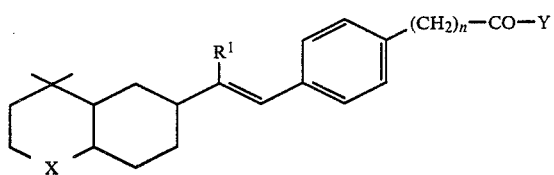

| X | R¹ | n | Y |
|---|---|---|---|
| O | CH₃ | 1 | CH(CH₃)₂ |
| O | H | 1 | CH₂(CH₂)₃CH₃ |
| O | CH₃ | 0 | C₆H₅ |
| S | CH₃ | 0 | CH₂CH₃ |
| S | H | 1 | CH₂CH₂CH(CH₃)₂ |
| S | H | 0 | CH₂CH₃ |
| SO | CH₃ | 1 | CH₃ |
| SO₂ | H | 0 | CH₂CH₃ |

EXAMPLE 4

Methyl 4-[(E)-2-(N-acetyl-4,4-dimethyl-1,2,3,4-tetrahydro-6-quinolinyl)-2-methylvinyl]benzoate Two drops of pyridine, followed by 3.28 g (0.012 mol) of phosphorus tribromide in 20 ml of ether, were added to 6.0 g (0.024 mol) of N-acetyl-4,4-dimethyl-6-(1-hydroxyethyl)-1,2,3,4-tetrahydroquinoline in 75 ml of ether, at 0° C., with stirring. Stirring was continued for 1 hour at 0° C., and then the reaction mixture was poured onto 100 g of ice. The resulting mixture was extracted with ether and the combined extracts were dried (MgSO₄) and then evaporated in vacuo. This gave 7.0 g of a white solid which was dissolved in 100 ml of toluene. To the resulting solution ws added 12.6 g (0.048 mol) triphenylphosphine, and then the mixture was refluxed for 18 hours, during which time the phosphonium salt precipitated as a viscous oil. The solvent was decanted from the oil, and then the latter was triturated under hot toluene. The toluene was removed by decantation, the residue was dissolved in dichloromethane, the dichloromethane was dried, and then the dichloromethane was removed by evaporation in vacuo. The residue (7.5 g, 0.013 mol), 2.15 g of methyl 4-formylbenzoate and 75 ml of 1,2-epoxybutane were heated under reflux for 48 hours. The reaction mixture was then evaporated in vacuo to give the title compound in admixture with the corresponding (Z)-isomer. The isomers were separated by column chromatography on silicic acid, eluting with etherhexane (1:1 by volume). The (E)-isomer (2.8 g) was further purified by recrystallization from etherhexane to give 2.3 g (25% yield) of the title compound, mp 141°–142° C.

The ¹H NMR spectrum (in CDCl₃) showed absorptions at 1.20 (s, 6H), 1.82 (t, 2H, J=6 Hz), 2.3 (d, 3H, J=1 Hz), 2.28 (s, 3H), 3.87 (t, 2H, J=6 Hz), 3.95 (s, 3H), 6.83 (s, 1H), 7.1–7.6 (m, 5H) and 8.1 (d, 2H) ppm.

Analysis: Calculated for C₂₄H₂₇NO₃: C, 76.36; H, 7.21; N, 3.71%. Found: C, 75.97; H, 7.13; N, 3.71%.

EXAMPLE 5

By reacting the appropriate alcohol of formula V with phosphorus tribromide followed by triphenylphosphine, and then coupling the phosphonium salt thus obtained with the requisite aldehyde of formula III, using the procedure of Example 4, the following compounds can be prepared:

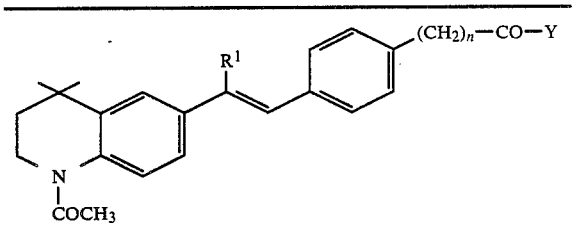

| R¹ | n | Y |
|---|---|---|
| CH₃ | 1 | CH₂CH(CH₃)₂ |
| H | 0 | CH₂(CH₂)₃CH₃ |
| CH₃ | 0 | C₆H₅ |
| H | 1 | CH₂CH₃ |

EXAMPLE 6

4-[(E)-2-(4,4-Dimethyl-6-chromanyl)-2-methylvinyl]benzoic Acid

Under a nitrogen atmosphere, a suspension of 10.9 g (32.4 mmol) of methyl 4-[(E)-2-(4,4-dimethyl-6-chromanyl)-2-methylvinyl]benzoate in 100 ml of ethanol was treated by dropwise addition of 100 ml of 6N potassium hydroxide, with stirring at 60° C. After 1 hour a clear solution resulted. The ethanol was removed by evaporation under reduced pressure, and 100 ml of water was added. The resulting mixture was acidified with 125 ml of concentrated hydrochloric acid, and the acidified mixture was extracted with dichloromethane. The combined extracts were dried (MgSO₄) and evaporated in vacuo to give 10.4 g (99% yield) of a solid. Recrystallization of 8.4 g of this solid yielded 5.6 g of the title compound, mp 179°–181° C.

The ¹H NMR spectrum of the product (in CDCl₃) showed absorptions at 1.38 (s, 6H), 1.82 (t, 2H, J=5 Hz), 2.27 (s, 3H), 4.17 (t, 2H, J=5 Hz), 6.7 (s, 1H), 6.73 (d, 1H, J=8 Hz), 7.1–7.47 (m, 4H) and 8.03 (d, 2H, J=8 Hz) ppm.

Analysis: Calcd. for C₂₁H₂₂O₃: C, 78.23; H, 6.88%. Found: C, 77.89; H, 6.91%.

EXAMPLE 7

Hydrolysis of the esters in the table in Example 2, using the procedure of Example 6, afforded the following compounds:

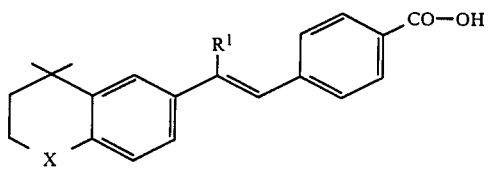

| X | R¹ | n | Melting Point (°C.) | Analysis Calculated | | | Analysis Found | | | NMR (ppm) (in CDCl₃) |
|---|---|---|---|---|---|---|---|---|---|---|
| | | | | C | H | S | C | H | S | |
| O | H | 0 | 257–258 | 77.90 | 6.54 | | 77.44 | 6.49 | | 1.38 (s, 6H), 1.83 (t, 2H, J=5 Hz), 4.17 (t, 2H, J=5 Hz), 6.63–7.37 (m, 5H), 7.68 (d of d, 4H, J=8 Hz and 28 Hz) |
| O | CH₃ | 1 | 158–159 | 78.54 | 7.19 | | 78.53 | 7.16 | | |
| S | CH₃ | 0 | 221–223 | 74.52 | 6.86 | 9.47 | 75.14 | 6.96 | 9.28 | |

EXAMPLE 8

By hydrolysis of the compounds in the table in Example 3, using the procedure of Example 6, the following compounds can be prepared:

| X | R¹ | n |
|---|---|---|
| O | CH₃ | 1 |
| O | H | 1 |
| O | CH₃ | 0 |
| S | CH₃ | 0 |
| S | H | 1 |
| S | H | 0 |
| SO | CH₃ | 1 |
| SO₂ | H | 0 |

EXAMPLE 9

4-[(E)-2-(N-Acetyl-4,4-dimethyl-1,2,3,4-tetrahydro-6-quinolinyl)-2-methylvinyl]benzoic Acid To a solution of 0.1 g (0.265 mmol) of methyl 4[(E)-2-(N-acetyl-4,4-dimethyl-1,2,3,4-tetrahydro-6-quinolinyl)-2-methylvinyl]benzoate in 10 ml of dioxane was added, with stirring, 0.8 ml (1.6 mmol) of 2N sodium hydroxide, with the temperature maintained at 25° C. Stirring was continued for 48 hours, and then the reaction mixture was diluted with 25 ml of water. It was then acidified to pH 2 with 2N hydrochloric acid and extracted with dichloromethane. The combined extracts were dried using sodium sulfate and then evaporated in vacuo to give the title compound as a white solid. The solid was recrystallized from methanol-hexane to give 70 mg of the title compound, mp 200°–202° C.

The infrared spectrum (as a KBr disc) showed absorptions at 1674 and 1649 cm⁻¹. The ¹H NMR spectrum (in CDCl₃) showed absorptions at 1.33 (s, 6H), 1.78 (t, 2H, J=6 Hz), 2.67 (m, 5H), 3.83 (t, 2H, J=6 Hz), 6.82 (bs, 1H), 7.2–7.6 (m, 5H) and 8.1 (d, 2H) ppm.

Analysis: Calcd. for C₂₃H₂₅NO₃: C, 75.94; H, 6.93; N, 3.85%. Found: C, 75.55; H, 6.93; N, 3.83%.

EXAMPLE 10

By hydrolysis of the compounds in the table in Example 5, using the procedure of Example 9, the following compounds can be prepared:

| R¹ | n |
|---|---|
| CH₃ | 1 |
| H | 0 |
| CH₃ | 0 |
| H | 1 |

EXAMPLE 11

4-[(E)-2-(4,4-Dimethyl-1,2,3,4-tetrahydro-6-quinolinyl)-2-methylvinyl]benzoic Acid To a solution of 0.1 g (0.265 mmol) of methyl 4-(E)-2-(N-acetyl-4,4-dimethyl-1,2,3,4-tetrahydro-6-quinolinyl)-2-methylvinyl]benzoate in 10 ml of hot ethanol is added 2.2 ml (13.2 mmol) of 6N potassium hydroxide, and the resulting solution was heated under reflux for 2 hours. The ethanol was removed by evaporation at atmospheric pressure, and the aqueous residue was adjusted to pH 6 with 1N hydrochloric acid. The precipitate which formed was collected by filtration, to give 0.07 g of the title compound.

The above product was dissolved in 50 ml of dichloromethane, and to this solution was added 50 ml of dichloromethane, which had been saturated with hydrogen chloride. The solvent was removed by evaporation in vacuo to give the title compound as its hydrochloride salt.

The ¹H NMR spectrum of the title compound (in CD₃OD) showed absorptions at 1.30 (s, 3H), 1.80 (t, 2H, J=5 Hz), 2.03 (d, 3H, J=3 Hz), 3.30 (m, 2H), 6.65 (bs, 1H) and 6.78–7.82 (m, 7H) ppm.

EXAMPLE 12

Potassium 4-[(E)-2-(4,4-dimethyl-1,2,3,4-tetrahydro-6-quinolinyl)-2-methylvinyl]benzoate To a solution of 0.125 g (0.33 mmol) of methyl 4-[(E)-2-(N-acetyl-4,4-dimethyl-1,2,3,4-tetrahydro-6-quinolinyl)-2-methylvinyl]benzoate in 10 ml of hot ethanol was added, dropwise, 2.75 ml of 6N potassium hydroxide, and the resulting solution was heated under reflux for 3 hours. The ethanol was removed by evaporation at atmospheric pressure, and then the residual aqueous solution was cooled. The solid which precipitated was collected by filtration to give 0.9 g of the title potassium salt, in admixture with the corresponding (Z)-isomer.

EXAMPLE 13

4-[(E)-2-(1-Oxo-4,4-dimethyl-6-thiochromanyl)-2-methylvinyl]benzoic Acid

To a stirred slurry of 0.695 g (3.25 mmol) of sodium metaperiodate in 10 ml of water at 0° C. was added, dropwise, under nitrogen, a solution of 1.0 g (2.95 ml) of 4-[(E)-2-(4,4-dimethyl-6-chromanyl)-2methylvinyl]benzoic acid in 25 ml of dioxane. The reaction mixture was stirred at 0° C. for 4 hours and then overnight at room temperature. The solid material was removed by filtration and the filtrate was partitioned between water and dichloromethane. The layers were separated and the aqueous layer was extracted with further dichloromethane. The combined organic solutions were dried using magnesium sulfate and then they were evaporated in vacuo to a solid. The solid was refluxed for 30 minutes in ether, and the insoluble material was recovered. The latter material was recrystallized from chloroform-ether followed by ethyl acetate-ethanol to give 0.23 g of the title compound, contaminated with some of its ethyl ester.

The above product was dissolved in a mixture of 5 ml of methanol and 2 ml of 6N potassium hydroxide, and this mixture was heated under reflux for 1 hour. The methanol was removed by evaporation at atmospheric pressure, the remaining solution was diluted with 20 ml of water, and then this latter solution was extracted with dichloromethane. The extracts were dried (MgSO$_4$) and evaporated in vacuo to give a solid. The solid was recrystallized from chloroformhexane to give 0.137 g of the title compound, mp 228-229.5.

The IR spectrum (KBr disc) showed an absorption at 1690 cm$^{-1}$.

Analysis: Calcd. for C$_{12}$H$_{22}$O$_3$S: C, 71.16; H, 6.26; S, 9.05%. Found: 68.73; H, 6.17; S, 8.68%.

EXAMPLE 14

4-[(E)-2-(1,1-Dioxo-4,4-dimethyl-6-thiochromanyl)-2-methylvinyl]benzoic Acid

To a stirred solution of 0.504 g (2.48 mmol) of 85% 3-chloroperbenzoic acid in 25 ml of chloroform at 0°-5° C., under nitrogen, was added, dropwise, a solution of 0.4 g (1.18 mmol) of 4-[(E)-2-(4,4-dimethyl-6-thiochromanyl)-2-methylvinyl]benzoic acid in 25 ml of chloroform. Stirring was continued overnight at 25° C., and then the reaction mixture was diluted with 100 ml of chloroform. The resulting solution was washed with saturated sodium bicarbonate solution and then the bicarbonate layer was extracted repeatedly with dichloromethane. The combined extracts were washed with 1N hydrochloric acid, followed by saturated sodium chloride solution, and then dried (MgSO$_4$) and evaporated. The solid so obtained (0.4 g, mp 242°-246° C.) was combined with a small amount of additional material of comparable quality and then it was recrystallized from ethanol. This afforded 0.23 g of the title product, mp 245°-247° C.

The IR spectrum (KBr disc) showed an absorption at 1690 cm$^{-1}$.

Analysis: Calcd. for C$_{21}$H$_{22}$O$_4$S: C, 68.08; H, 5.99; S, 8.66%. Found: C, 67.41; H, 6.00; S, 8.33%.

EXAMPLE 15

Methyl 4-[(E)-2-(N,4,4-Trimethyl-1,2,3,4-tetrahydro-6-quinolinyl)-2-methylvinyl]benzoate A mixture of 3.64 g of methyl 4-[(E)-2-(4,4-dimethyl-1,2,3,4-tetrahydro-6-quinolinyl)-2-methylvinyl]benzoate, 5 ml of 90% formic acid and 5 ml of 40% aqueous formaldehyde is heated at 95° C. for 12 hours. The reaction medium is then cooled and 1.5 ml of concentrated hydrochloric acid is added. The formic acid and excess formaldehyde are removed by evaporation in vacuo. The resulting mixture is then made strongly basic and extracted with dichloromethane. The dichloromethane extracts are combined, dried (MgSO$_4$) and evaporated in vacuo to give the title compound.

EXAMPLE 16

4-(E)-2-(4,4-Dimethyl-6-chromanyl)-2-methylvinyl]-benzamide

Ammonia gas was bubbled into a 15 ml aliquot of the chloroform solution of the mixed anhydride of 4-(E)-2-(4,4-dimethyl-6-chromanyl)-2-methylvinyl]benzoic acid from Preparation 13 at 0° C. The chloroform solution was then filtered and extracted with 1N hydrochloric acid. The resulting solution was dried (MgSO$_4$) and evaporated in vacuo to give a white solid. The solid was chromatographed twice on silica gel (eluting firstly with 19:1 toluene-ethanol containing 0.5% acetic acid, and secondly with 49:1 toluene-ethanol containing 0.5% acetic acid). This afforded the crude title product, mp 178°-180° C. The crude product was recrystallized from methanol-hexane to give 0.05 g of the title compound, mp 181°-182° C.

Analysis: Calcd. for C$_{21}$H$_{23}$NO$_2$: C, 78.47; H, 7.21; N, 4.36%. Found: C, 78.56; H, 7.20; N, 4.30%.

EXAMPLE 17

N-n-Propyl-4-[(E)-2-(4,4-dimethyl-6-chromanyl)-2-methylvinyl]benzamide

A 15 ml aliquot of the chloroform solution of the mixed anhydride of 4-[(E)-2-(4,4-dimethyl-6-chromanyl)-2-methylvinyl]benzoic acid from Preparation 13 was added to a solution of 0.1 g (1.71 mmole) of n-propylamine in ca. 25 ml of chloroform at 0° C. The reaction mixture was filtered and then it was extracted twice with 1N hydrochloric acid. The resulting chloroform solution was dried (MgSO$_4$) and evaporated in vacuo to give an oily solid. This solid was dissolved in diethyl ether and 2N sodium hydroxide. The layers were separated and the ether layer was filtered, dried (MgSO$_4$) and evaporated in vacuo. The residue was recrystallized from diethyl ether-hexane, to give 0.127 g of the title compound, mp 138°-139° C.

Analysis: Calcd. for $C_{24}H_{29}NO_2$: C, 79.30; H, 8.04; N, 3.85%. Found: C, 79.04; H, 8.21; N, 3.84%.

EXAMPLE 18

N-[4-Hydroxyphenyl-4-[(E)-2-(4,4-dimethyl-6-chromanyl)-2-methylvinyl]benzamide

A 15 ml aliquot of the chloroform solution of the mixed anhydride of 4-[(E)-2-(4,4-dimethyl-6-chromanyl)-2-methylvinyl]benzoic acid from Preparation 13 was added to a solution of 0.187 g (1.71 mmole) of 4-aminophenol in ca. 25 ml of chloroform/dioxane. The organic solution was then extracted twice with 1N hydrochloric acid, dried (MgSO$_4$) and then concentrated in vacuo to a viscous oil. The oil was purified by chromatography on silica gel, eluting with toluene-ethanol 99:1 containing 0.5% acetic acid, followed by recrystallization from methanol-hexane, to give the title compound, mp 187°–188°.

Analysis: Calcd. for $C_{27}H_{27}NO_3$: C, 78.42; H, 6.58; N, 3.38%. Found: C, 78.04; H, 6.51; N, 3.43%.

EXAMPLE 19

N-Phenyl-4-[(E)-2-(4,4-dimethyl-6-chromanyl)-2-methylvinyl]benzamide

The title compound can be prepared by converting 4-[(E)-2-(4,4-dimethyl-6-chromanyl)-2methylvinyl]benzoic acid into a mixed anhydride using ethyl chloroformate according to the procedure of Preparation 13, followed by reaction with aniline according to the procedure of Example 18.

EXAMPLE 20

N-[5-Tetrazolyl]-4-[(E)-2-(4,4-dimethyl-6-chromanyl)-2-methylvinyl]benzamide

To a stirred solution of 0.5 g (1.55 mmole) of 4-[(E)-2-(4,4-dimethyl-6-chromanyl)-2-methylvinyl]benzoic acid in 20 ml of chloroform-N,N-dimethylformamide (1:1) at −25° C., under nitrogen, was added 0.17 g of triethylamine followed by 0.23 g (1.7 mmole) of isobutyl chloroformate. Stirring was continued for 15 minutes at −25° C. and then a solution of 0.177 g (1.7 mmole) of 5-aminotetrazole in 4 ml of N,N-dimethylformamide was added dropwise during 2 minutes. Stirring was continued for 1 hour as the reaction mixture was allowed to warm to 25° C. The reaction mixture was then diluted with 50 ml of chloroform and washed with 50 ml of 1N hydrochloric acid. The insoluble material was recovered by filtration to give a first crop of the title compound. The layers were then separated and the chloroform layer was washed with 1N hydrochloric acid followed by saturated sodium chloride, dried (MgSO$_4$) and concentrated in vacuo. The residue was triturated under hot chloroform and the insoluble material was collected by filtration to give a second crop of the title compound.

The two crops of the title compound were combined and recrystallized from methanol to give a solid, mp greater than 250° C.

Analysis: Calcd. for $C_{22}H_{23}N_5O_2$: C, 67.85; H, 5.95; N, 17.98%. Found: C, 67.48; H, 6.05; N, 17.88%.

PREPARATION 1

1-(4,4-Dimethyl-6-chromanyl)ethyltriphenylphosphonium Bromide

A solution of 6.0 g (22.3 mmol) of 4,4-dimethyl-6-(1-bromoethyl)chrman and 7.07 g (27.8 mmol) of triphenylphosphine in 100 ml of toluene was heated at 100° C. for 72 hours. The resulting solution was concentrated to an oil, diluted with methanol and absorbed onto 50 g of silicic acd. This latter material was then placed on top of 200 g of additional silicic acid contained in a funnel, and the total silicic acid was washed with several volumes of methanol. The first material to be eluted from the silicic acid was triphenylphosphine, followed by the title compound. Evaporation of the product-containing methanol in vacuo afforded 2.1 g (17% yield) of the title compound as a white, very hygroscopic solid, which was stored under nitrogen.

The $^1$H NMR spectrum (in CDCl$_3$) showed absorptions at 1.10 (s, 3H), 1.13 (s, 3H), 1.73 (t, 2H, J=5 Hz), 1.80 (dd, 3H, J=19 Hz, J$_2$=7 Hz), 4.13 (t, 2H, J=5 Hz), 5.98–6.6 (m, 1H) and 6.6–8.0 (m, 18H) ppm.

PREPARATION 2

6-(1-Bromoethyl)-4,4-dimethylchroman

To a stirred solution of 6.0 g (29.1 mmol) of 4,4-dimethyl-6-(1-hydroxyethyl)chroman and 1.15 g (14.5 mmol) of pyridine in 25 ml of hexane, was added 3.92 g (14.5 mmol) of phosphorus tribromide, at ca. 0° C. Stirring was continued at ca. 0° C. for 1 hour, and then the reaction mixture was poured into 500 ml of diethyl ether. The ether was washed with water, dried (MgSO$_4$) and evaporated in vacuo to give 6.0 g (78% yield) of the title compound as an oil.

The $^1$H NMR spectrum (in CDCl$_3$) showed absorptions at 1.33 (s, 6H), 1.75 (t, 2H, J=5 Hz), 1.97 (d, 3H, J=7 Hz), 4.1 (t, 2H, J=5 Hz), 5.13 (q, 2H, J=7 Hz), 6.63 (d, 1H, J=8 Hz) and 6.97–7.23 (m, 2H) ppm.

PREPARATION 3

4,4-Dimethyl-6-(1-hydroxyethyl)chroman

To a solution of 6.0 g of 6-acetyl-4,4-dimethylchroman in 50 ml of methanol was added, all in one portion, with stirring, 3.78 g of sodium borohydride at ca. 0° C. Stirring was continued at ca. 0° C. for 1.5 hours, and then the reaction mixture was poured into 500 ml of saturated sodium chloride solution. The resulting mixture was extracted with diethyl ether, and the combined ether extracts were dried (MgSO$_4$) and evaporated in vacuo to give 6.0 g of the title compound as an oil.

The $^1$H NMR spectrum showed absorptions at 1.33 (s, 6H), 1.47 (d, 3H, J=6 Hz), 1.8 (t, 2H, J=5 Hz), 4.13 (t, 2H, J=5 Hz), 4.77 (q, 1H, J=6 Hz), 6.67 (d, 1H, J=8 Hz), 7.0 (dd, 1H, J$_1$=8 Hz, J$_2$=2H Hz) and 7.2 (d, 1H, J=2 Hz) ppm.

PREPARATION 4

6-Acetyl-4,4-dimethylchroman

To a mixture of 16.3 g (122 mmol) of aluminum chloride, 11.77 g (10.7 mmol) of acetyl chloride and 110 ml of carbon disulfide was added, slowly, with stirring, 18.0 g (111 mmol) of 4,4-dimethylchroman, at 0 to 5° C. After the addition was complete, stirring was continued for 4 hours at 0° C. The mixture was then poured onto 200 ml of 6N hydrochloric acid and 200 g of ice. The resulting mixture was extracted with 500 ml of diethyl ether. The ether extract was dried (MgSO$_4$) and evaporated in vacuo to give an oil, which was fractionally distilled, under reduced pressure, to give 6.99 g (31% yield) of the title compound, bp 110°–113° C. (0.03 mm Hg).

The $^1$H NMR spectrum (in CDCl$_3$) showed absorptions at 1.38 (s, 6H), 1.82 (t, 2H, J=6 Hz), 2.43 (s, 3H), 4.23 (t, 2H, J=6 Hz), 6.88 (d, 1H, J=8 Hz), 7.65 (dd, 1H, J$_1$=8 Hz, J$_2$=2 Hz) and 7.93 (d, 1H, J=2 Hz) ppm.

PREPARATION 5

4,4-Dimethylchroman

A mixture of 19.2 g 2-methyl-4-phenoxy-1-butene and 50 ml of anhydrous hydrogen fluoride was stored at room temperature for 3 days. The mixture was then diluted with 500 ml of diethyl ether and the resulting mixture was washed with saturated sodium bicarbonate solution (2×500 ml). It was then dried (MgSO$_4$) and concentrated in vacuo to give 17.7 g of the title compound as an oil. Yield 92%.

The $^1$H NMR spectrum (in CDCl$_3$) showed absorptions at 1.33 (s, 6H), 1.75 (t, 2H, J=6 Hz), 4.13 (t, 2H, J=6 Hz) and 6.47–7.27 (m, 4H) ppm.

PREPARATION 6

2-Methyl-4-phenoxy-1-butene

A mixture of 24.4 g (260 mmol) of phenol, 47.0 g (286 mmol) of 2-methyl-4-methylsulfonyloxy-1-butene, 107 g (780 mmol) of potassium carbonate and 300 ml of N,N-dimethylformamide was stirred and heated at 80° C. for 6 hours, and then it was poured onto 500 ml of ice-water. The resulting mixture was extracted with hexane and the combined extracts were dried (MgSO$_4$) and evaporated in vacuo to give the title compound as an oil (28.0 g, 66% yield).

The $^1$H NMR spectrum of the product (in CDCl$_3$) showed absorptions at 1.73 (s, 3H), 2.4 (t, 2H, J=6 Hz), 3.92 (t, 2H, J=6 Hz), 4.75 (s, 2H) and 6.62–7.25 (m, 5H) ppm.

PREPARATION 7

2-Methyl-4-methylsulfonhloxy-1-butene

To a stirred solution of 25 g (290 mmol) of 2-methyl-4-hydroxy-1-butene and 50.5 g (500 mmol) of triethylamine in 200 ml of dichloromethane was added, dropwise, with cooling to −3° to −5° C., 36.4 g (319 mmole) of methanesulfonyl chloride. Stirring was continued for 1 hour and then the reaction mixture was poured onto 500 ml ice-water. The organic layer was removed and washed with 10% hydrochloric acid (500 ml) followed by saturated sodium chloride (500 ml). The organic layer was then dried (MgSO$_4$) and evaporated in vacuo to give 47 g (89% yield) of the title compound as an oil.

The $^1$H NMR spectrum (in CDCl$_3$) showed absorptions at 1.73 (s, 3H), 2.45 (t, 2H, J=6 Hz), 2.98 (s, 3H), 4.27 (t, 2H, J=6 Hz) and 4.78 (bs, 2H) ppm.

PREPARATION 8

N-Acetyl-4,4-dimethyl-6-(1-hydroxyethyl)-1,2,3,4-tetrahydroquinoline

To a stirred solution of 17.8 g (0.088 mol) of N-acetyl-4,4-dimethyl-1,2,3,4-tetrahydroquinoline in 100 ml of carbon disulfide at 25° C. was added 68.1 g (0.512 mol) of aluminum chloride over a 30 minute period. To this mixture was then added 21.9 g (0.28 mol) of acetyl chloride at such a rate that a gentle reflux was maintained. Following the latter addition, refluxing was continued for 4 hours and then the mixture was stirred overnight. Then, to the mixture was added 500 g of ice, and the aqueous system was extracted with ether. The combined extracts were washed with sodium bicarbonate and then they were dried (MgSO$_4$) and evaporated in vacuo. The residue was chromatographed on silicic acid, eluting with ether-hexane (3:7, volume per volume), to give 9.1 g of a mixture of 6,N-diacetyl-4,4-dimethyl-1,2,3,4-tetrahydroquinoline and 8,N-diacetyl-4,4-dimethyl-1,2,3,4-tetrahydroquinoline.

The latter mixture was dissolved in methanol, the resulting solution was cooled to 0° C. and then 4.0 g (0.105 mmol) of sodium borohydride was added. This mixture was stirred at 0° C. for 1 hour. The reaction mixture was then evaporated to one half the original volume, the organic phase was dried over magnesium sulfate and finally concentrated in vacuo. The residue was chromatographed on silicic acid, eluting with chloroform-ethanol (99:1, volume per volume), which gave 6.0 g (28% yield) of the title compound as a clear oil.

The $^1$H NMR spectrum (in CDCl$_3$) showed absorptions at 1.30 (s, 6H), 1.48 (d, 2H, J=7 Hz), 1.73 (t, 2H, J=6 Hz), 2.20 (s, 3H), 3.77 (t, 2H, J=6 Hz), 4.82 (m, 1H) and 7.0–7.3 (m, 3H) ppm.

PREPARATION 9

N-Acetyl-4,4-dimethyl-1,2,3,4-tetrahydroquinoline

To a stirred solution of 15 g (0.93 mol) of 4,4-dimethyl-1,2,3,4-tetrahydroquinoline in 50 ml of pryidine, at 0° C., was added, dropwise, 14.5 g (0.185 mol) of acetyl chloride over a 30 minute period. Stirring was continued at 0° C. for 1 hour, and then the reaction mixture was poured onto 200 g of ice. The resulting mixture was extracted with ether. The combined organic extracts were washed successively with 1N hydrochloric acid and saturated sodium bicarbonate and then they were dried using magnesium sulfate. Evaporation of the ether solution in vacuo afforded 18.8 g (99% yield) of the title compound as a yellow oil.

The $^1$H NMR spectrum (in CDCl$_3$) showed absorptions at 1.3 (s, 6H), 1.8 (t, 2H, J=6 Hz), 2.2 (s, 3H), 3.8 (t, 2H, J=6 Hz) and 7.0–7.4 (m, 4H) ppm.

PREPARATION 10

4,4-Dimethyl-1,2,3,4-tetrahydroquinoline

To a refluxing suspension of 10 g (0.26 mol) of lithium aluminum hydride in 100 ml of ether was added dropwise over a period of 1 hour a solution of 21.0 g (0.21 mol) of 4,4-dimethyl-2-oxo-1,2,3,4-tetrahydroquinoline in 200 ml of ether-tetrahydrofuran (2:1, volume per volume). Refluxing was continued for 16 hours, and then to the cooled reaction mixture was added 50 ml of water and 50 ml of 10% sodium hydroxide. The aqueous phase was extracted with ether, and the combined ether extracts were dried (MgSO$_4$) and evaporated in vacuo to give 17.2 g (89% yield) of the title compound as a clear oil.

The $^1$H NMR spectrum (in CDCl$_3$) showed absorptions at 1.30 (s, 6H), 1.7 (t, 2H, J=6 Hz), 3.25 (t, 2H, J=6 Hz) and 6.3–7.2 (m, 4H) ppm.

PREPARATION 11

4,4-Dimethyl-2-oxo-1,2,3,4-tetrahydroquinoline

To 40 g (0.22 mol) of 3-methylcrotonoanilide, heated in the molten state at 130° C., was added 33.4 g (0.25 mol) of aluminum chloride, portionwise, over a 30 minute period. Heating was continued at 130° C. for a further 30 minutes, and then the temperature was lowered to 85° C. and a further 5 g (0.038 mol) of aluminum chloride was added. The temperature was maintained at 85° C. for 1 hour and then the reaction mixture was treated cautiously with 500 g of ice. The resulting mixture was extracted with ether and the ether extracts were dried (MgSO4) and evaporated in vacuo. The residue was chromatographed on silicic acid, eluting with ether:hexane (1:2), and the product containing fractions were combined and evaporated in vacuo. This afforded 23.7 g (59% yield) of the title compound, mp 111°–112° C.

The $^1$H NMR spectrum of the product showed absorptions at 1.33 (s, 6H), 2.48 (s, 2H) and 6.7–7.3 (m, 4H) ppm.

PREPARATION 12

3-Methylcrotonoanilide

To a stirred solution of 4.1 g (0.44 mol) of aniline in 200 ml of chloroform, at 25° C., was added slowly a solution of 25 g (0.21 mol) of 3-methylcrotonoyl chloride in 100 ml of chloroform. The reaction mixture was refluxed for 1.5 hours, and then the precipitate was removed by filtration. The chloroform solution was washed successively with 1N hydrochloric acid and saturated sodium bicarbonate solution, and then it was dried (MgSO4) and evaporated in vacuo. This gave 33.5 g (91% yield) of the title compound as a solid, mp 122°–125° C.

The $^1$H NMR spectrum (in CDCl3) of the product showed absorptions at 1.85 (d, 3H, J=2 Hz), 2.20 (d, 2H, J=2 Hz), 5.6–5.8 (m, 1H) and 6.9–7.2 (m, 5H) ppm.

PREPARATION 13

Mixed Anhydride of 4-[(E)-2-(4,4-dimethyl-6-chromanyl)-2-methylvinyl]-benzoic Acid To a stirred solution of 2.0 g (6.21 mmole) of 4-[(E)-2-(4,4-dimethyl-6-chromanyl)-2-methylvinyl]benzoic acid in 60 ml of chloroform at −20° to −30° C. was added 0.69 g (6.83 mmole) of triethylamine. Stirring was continued for 5 minutes, and then 0.74 g (6.83 mmole) of ethyl chloroformate was added dropwise over 2 minutes. Stirring was continued at −25° C. for 40 minutes to give a chloroform solution of the title mixed anhydride.

PREPARATION 14

6-Bromomethyl-4,4-dimethylchroman

A mixture of 5.0 g (28.4 mmole) of 4,4,6-trimethylchroman, 5.55 g of purified N-bromosuccinimide and 200 ml of carbon tetrachloride was heated under reflux for 12 hours. The succinimide was removed by filtration and the solvent was removed by evaporation in vacuo to give the title compound as a light yellow oil.

PREPARATION 15

(4,4-Dimethyl-6-chromanyl)methyltriphenylphosphonium Bromide

A mixture of 7.25 g (28.4 mmole) of 6-bromomethyl-4,4-dimethylchroman, 14.8 g (56.8 mmole) of triphenylphosphine and 100 ml of toluene were heated under reflux for 12 hours, and then the solvent was removed by evaporation in vacuo. The residue (an oil) was dissolved in dichloromethane and decolorized with activated carbon. The solvent was removed by evaporation in vacuo and the residue was triturated under hexane to remove starting materials. The product so obtained was recrystallized from toluene-chloroform and the solid was discarded. The recrystallization mother liquors were evaporated in vacuo and the oily residue was triturated under 1N hydrochloric acid and then dissolved in dichloromethane. This latter solution was dried (MgSO4) and evaporated in vacuo to give 5.2 g of the title compound as a light brown solid.

PREPARATION 16

1-(4,4-Dimethyl-6-thiocromanyl)ethyltriphenylphosphonium Bromide

To a stirred solution of 29.2 g (0.13 mole) of 4,4-dimethyl-6-(1-hydroxyethyl)thiochroman in 150 ml of diethyl ether containing 3 drops of pyridine, at 0° C., under nitrogen, was added dropwise during 1 hour, 17.6 g (0.065 mole) of phosphorus tribromide in 50 ml of diethyl ether. Stirring was continued for 0.5 hour and then the reaction mixture was poured onto 400 ml of ice-water. The resulting mixture was extracted with diethyl ether, and the extracts were dried (MgSO4) and evaporated in vacuo to give an oil. This oil, and 68 g of triphenylphosphine, were heated under reflux in 200 ml of toluene for 15 hours. After cooling, the supernatant toluene was removed by decantation, and the residue was triturated under hot toluene. Finally the residue was dissolved in dichloromethane, the solution was dried using magnesium sulfate, and evaporation in vacuo afforded 60.9 g of the title phosphonium salt.

We claim:

1. A method of inhibiting the degradation of cartilage in a joint of a mammalian subject afflicted with an arthritic disease, which comprises administering to said subject a cartilage degradation inhibiting amount of a compound of the formula

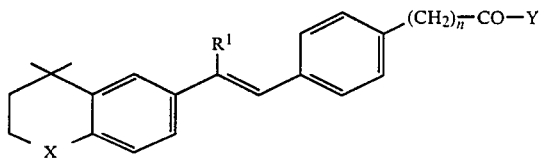

or a pharmaceutically-acceptable acid-addition salt thereof or a pharmaceutically-acceptable base salt thereof, wherein X is selected from the group consisting of O, S, SO, SO2 and NR$^2$;

R$^1$ is selected from the group consisting of H and CH3;

Y is selected from the group consisting of OH, OR$^3$ and NHR$^4$; and n is zero or one; wherein R$^2$ is selected from the group consisting of H, CH and CO-CH3;

R$^3$ is selected from the group consisting of alkyl having 1 to 5 carbons and phenyl;

and R$^4$ is selected from the group consisting of H, alkyl having 1 to 5 carbons, phenyl, hydroxyphenyl and 5-tetrazolyl.

2. The method of claim 1, wherein X is O.

3. The method of claim 2, wherein R$^1$ is CH3.

4. The method of claim 3, wherein Y is OH and n is zero.

5. The method of claim 3, wherein Y is OCH3 and n is zero.

6. The method of claim 1, wherein X is selected from the group consisting of S, SO and SO2.

7. The method of claim 6, wherein X is S.

8. The method of claim 7, wherein R$^1$ is CH3, Y is OH and n is zero.

9. The method of claim 7, wherein Rl is CH3, Y is OCH3 and n is zero.

10. The method of claim 1, wherein X is NR$^2$.

11. The method of claim 10, wherein X is N—CO—CH3, R$^1$ is CH3, Y is OH and n is zero.

12. The method of claim 10, wherein X is N—CO—CH3, R$^1$ is CH3, Y is OCH3 and n is zero.

* * * * *